(12) United States Patent
Bayerl et al.

(10) Patent No.: US 6,868,343 B1
(45) Date of Patent: Mar. 15, 2005

(54) INTERACTIONS BETWEEN SUBSTANCES AND SURFACES THAT ARE MADE UP OF AMPHIPHILIC MOLECULES

(75) Inventors: Thomas Bayerl, Wuerzburg (DE); Angelika Loidl-Stahlhofen, Leipzig (DE); Matthias Schoettner, Bayreuth (DE)

(73) Assignee: NIMBUS Biotechnologie GmbH, Leipzig (DE)

( * ) Notice: Subject to any disclaimer, the term of this patent is extended or adjusted under 35 U.S.C. 154(b) by 0 days.

(21) Appl. No.: 09/647,559

(22) PCT Filed: Apr. 1, 1999

(86) PCT No.: PCT/EP99/02260

§ 371 (c)(1),
(2), (4) Date: Dec. 13, 2000

(87) PCT Pub. No.: WO99/51984

PCT Pub. Date: Oct. 14, 1999

(30) Foreign Application Priority Data

Apr. 2, 1998 (DE) .......................................... 198 14 775

(51) Int. Cl.$^7$ ......................... G01N 33/48; G01N 31/00; G01N 33/566; G06F 19/00
(52) U.S. Cl. ............................. 702/23; 702/19; 436/501
(58) Field of Search ...................... 702/19, 23; 436/501

(56) References Cited

U.S. PATENT DOCUMENTS

| 5,094,819 A | 3/1992 | Yager et al. ............. 422/82.07 |
| 5,670,631 A | 9/1997 | Bayerl et al. ............... 530/412 |

OTHER PUBLICATIONS

Loidl–Stahlhofen et al. The thermodynamic control of protein binding to lipid bilayers for protein chromatography. Nature Biotechnology. Aug. 1996. vol. 14, No. 8, pp. 999–1002.*

Obringer AR, et al, "Antiphospholipid Antibody Binding to Bilayer–Coated Glass Microspheres", Journal of Immunological Methods, 185 1 (1995) pp 81–93.

Miyake K, et al, "Phosphatidyl–choline–Coated Silica as a Useful Stationary Phase for High Performance Liquid Chromatography Determination of partition Coefficients Between Octanol and Water" Journal of Chromatography, 389 (1987) pp 47–56.

Beigi F, et al, "Immobilized–liposome Chromatographic Analysis of Drug Partitioning Into Lipid Bilayers", Journal of Chromatography, 704 (1995) pp 315–321.

Linseisen FM, et al, "Differences in the Physical Properties of Lipid Monolayers and Bilayers on a Spherical Solid Support", Biophysical Journal 72(1997) pp 1659–1667.

Reinl HM, et al, "Interaction of Myelin Basic Protein with Single Bilayers on a Solid Support: an NMR, DSC and Polarized Infrared ATR Study", Biochimica et Biophysica Acta, 1151 (1993) pp 127–136.

Naumann C, et al, "Phase Transition Behavior of Single Phosphatidylcholine Bilayers on a Solid Spherical Support Studied by DSC, NMR and FT–IR", Biophysical Journal 63, (1992) pp 1314–1319.

Ong S et al, "Membrane Partition Coefficients Chromatographically Measured Using Immobilized Artificial Membrane Surfaces", Analytical Chemistry 67 (1995), pp 755–762.

Tamm L, et al, "Supported Phospholipid Bilayers", Biophysical Journal, 47, (1985) pp 105–113.

Lundqvist A, et al, "Chromatography on Cells and Biomolecular Assemblies", Journal of Chromatography B 699 (1997), pp 209–220.

Vergeres G, et al, "Binding of Myristoylated Alanine–rich C Kinase Substrate–related Protein (MRP) to Vesicular Phospholipid membranes", Biochem. J. 330 (1998) pp 5–11.

* cited by examiner

Primary Examiner—Marianne P. Allen
Assistant Examiner—Channing S. Mahatan
(74) Attorney, Agent, or Firm—Antonelli, Terry, Stout & Kraus, LLP

(57) ABSTRACT

The invention relates to the analysis of interactions of substances or materials with surfaces or interfaces made from amphiphilic materials and in particular partition coefficients and/or binding constants are determined. For this purpose use is made of a carrier material, which is so coated with amphiphilic molecules in the so-called fluid phase that the lateral diffusion of the amphiphilic molecules is substantially unimpeded.

The invention also relates to a kit suitable for such analyses, and to a process for analyzing these interactions in column chromatography, particularly high pressure or performance liquid chromatography.

19 Claims, No Drawings

INTERACTIONS BETWEEN SUBSTANCES AND SURFACES THAT ARE MADE UP OF AMPHIPHILIC MOLECULES

The invention firstly relates to a process for analyzing interactions of substances or materials with surfaces or interfaces from amphiphilic molecules, as well as the use of a coated carrier material for analyzing said interactions and a kit suitable for performing the process according to the invention.

The determination of binding constants of water-soluble molecules on amphiphilic surfaces or interfaces (particularly lipid membranes) is of increasing significance in pharmacology, medicine, biotechnology and biochemistry. It provides detailed information of how molecules (particularly biomolecules such as e.g. peptides, proteins or nucleic acids, but also biologically active substances and agents) interact with biological membranes, how they are transported within cells and how they can evolve their signal action. The knowledge of lipid binding constants or the corresponding partition coefficients is indispensable for the development of therapeutically active biomolecules and other new medicaments (Böhm, H. J., Klebe, G., Kubinyi, H., "Wirkstoffdesign", Spektrum, Akad. Verl., 1st edition, Heidelberg (1996)).

In the specific case of pharmaceuticals use has hitherto been made of the approximation of a partition coefficient between the alcohol octanol and water, the so-called Kow value in order to characterize the lipid affinity (Fujita, T., Iwasa, J., Hansch, C. "A new substituent constant, derived from partition coefficients", J. Am. Chem. Soc. 86, 5175–5180 (1994)).

From the tendency of a compound to stay in the nonpolar alcohol phase conclusions are drawn concerning its lipid solubility. However, biological membranes are nanostructured, quasi-two dimensional objects, whose complex characteristics can only be very inadequately imitated by the octanol/water interface. As a more realistic model system use has been made of lipid monolayers at the water/air interface of a Langmuir tank for measuring the lipid binding of active agents (Seelibu, A. "Local anestetics and pressure: a comparison of dibucaine binding to lipid monolayers and bilayers", Biochim. Biophys. Acta 899, 196–204 (1997)).

The prerequisite for the quantification of binding phenomena on biological membranes are precisely defined lipid membrane model systems. According to the present state of the art three different systems are used for this purpose: (1) lipid vesicles, which can be produced with different standard methods (Mayer L. D., Hope, M. J., Cullis, P. R. "Vesicles of variable sizes produced by a rapid extrusion procedure", Biochim. Biophys. Acta 858, 161–168 (1986)), (2) planar lipid layers (so-called lipid monolayers), which can be prepared by Langmuir-Blodgett methods (Adamson, A. W., Gast, A. P., "Physical Chemistry of Surfaces", Ch. XV., pp 557–562, Wiley Interscience New York (1997)) and (3) on solids by the covalent bonding of immobilized lipid layers (so-called immobilized membranes) (Onbo, S., Liu, X, Qiu, X, Bhat, G, Pidgeon, C., "Membrane Partition Coefficients Chromatographically Measured Using Immobilized Artificial Membrane Surfaces", Anal. Chem. 67, 755–762 (1995)).

All these systems suffer from system-specific disadvantages. Lipid vesicles are unstable and in particular have a tendency to fusion or aggregation and consequently do not permit a reliable estimation of the surface exposed with respect to the molecules to be analyzed. In addition, the molecules to be analyzed can, during binding, influence the morphology of the lipid vesicles (e.g. induction of a vesicle fusion), so that it is even more difficult to quantify the binding.

For lipid monolayers a problem exists regarding the comparatively small surface which can be exposed to the molecules to be analyzed, so that binding detection is made more difficult. A further lipid monolayer problem is its inhomogeneity (formation of defects or demixions), because variations from a homogeneous distribution of the lipids can influence the binding of the molecule at the surface.

Immobilized membranes suffer from the disadvantage that each lipid molecule is covalently anchored to the solid surface. This is not only a technically more complicated and therefore more expensive process, but in the case of a multicomponent immobilized lipid mixture it suffers from the disadvantage that during immobilization there can be a cluster formation of similar lipids as a result of demixing. Consequently immobilized membranes in the case of complex lipid mixtures can have surface heterogeneities, which can falsify the measured result. The problem here is in connection with the covalent bonding to the solid, because as a result the lateral diffusivity of the lipids in the plane of the membrane, which is a characteristic of any natural membrane, is completely prevented. Thus, once heterogeneities have formed they cannot be compensated by molecular diffusion. The complicated preparation procedure for immobilized membranes also prevents a rapid adaptation of the lipid composition on the surface to the composition desired for the specific experiment.

Lipid binding constant determination processes based on these model systems consequently require numerous time-consuming control experiments, in order to expose in the actual experiment precisely defined quantities of lipids and surfaces. The necessary measuring methods for quantifying in the next step the binding of the molecule to be analyzed to the model membrane can be placed in two categories.

Firstly an attempt can be made to directly determine the binding between the (bio)molecule and the model membrane. For this purpose use is e.g. made of spectroscopic measuring methods such as fluorescence spectroscopy (Fedoreeva, L. I., Solov'eva, T. F., "Binding of porin with lipopolysaccharide from *Yersinia pseudotuberculosis*", Biorg. Khim. 21, 17–23 (1995)), circulardichroism (Terzi, B., Holzemann, G., Seelig, J., "Self-association of beta-amyloid peptide (140) in solution and binding to lipid membranes", J. Mol. Biol. 252:5 633–42 (1995)), plasmon resonance spectroscopy (Salamon, Z., Macleod, A., Tollin, G., "Surface plasmon resonance spectroscopy as a tool for investigating the biochemical and biophysical properties of membrane protein systems, II Applications to biological systems, Biochim. Biophys. Acta 1331, 131–152 (1997)) or Infrared spectroscopy (Reinl, H. M., Bayerl, T. M. "Interaction of myelin basic protein with single bilayers on a solid support: an NMR, DSC and polarized infrared ATR study", Biochim. Biophys. Acta 1151, 127–136 (1993)). In addition, conclusions concerning binding phenomena can be drawn from the change to the heat of reaction (isothermal titration calorimetry) (Beschiavili, G., Seelig, J. "Peptide Binding to Lipid Bilayers. Nonclassical Hydrophobic Effects and Membrane-Induced pH shifts" Biochemistry 31, 10044–10053 (1992)), the potential at the membrane surface or the surface tension (Lakhdar-Ghazdal, F., Vigroux, Willson, M., Tocanne, J. F. Périé., J., Faye, J. C. "Interactions between trypanocidal drugs and membrane phospholipids. A surface pressure, surface potential and electrophoretic mobility study", Biochem. Pharmacol. 42(11), 2099–2105 (1991)). The problems of these measuring methods, which are very complicated from the apparatus standpoint is to find a suitable, readily detectable measurement signal, which is clearly correlated with the membrane binding and on which is not superimposed other molecular phenomena. The mathematical evaluation of the measured data is consequently complex and generally requires numerous simplifying and not always plausible assumptions.

The second method obviates to a partial extent the aforementioned measurement problems in that for quantifying the binding following incubation the bound molecules are separated from the unbound molecules in spatial manner and into different compartments, where it is possible to determine the concentrations of the molecules separately using suitable measuring procedures (e.g. radioactivity, mass spectroscopy, activity tests, UV/VIS spectroscopy). However, the precision is very limited as a result of the above-discussed membrane model characteristics. For separating the available lipid vesicle systems it is necessary to use very time-intensive methods such as equilibrium dialysis, gel filtration or ultracentrifugation. For speeding up the long sedimentation times in ultracentrifugation of lipid vesicles their density is frequently increased by charging the inner volume with sucrose or suitable polymers (Vergeres, G., Ramsden, J. J., "Binding of myristoylated alanine-rich C kinase substrate-related protein (MRP) to vesicular phospholipid membranes", Biochem. J. 330, 5–11, (1998)), which reduces the stability of the system and consequently considerably increases the artifact susceptibility of the method.

For the use of lipid monolayers or Langmuir-Blodgett layers as the membrane model, if the separation in different compartments is successful, only a few and technically very complicated methods are able to provide the necessary sensitivity when detecting the molecules. This is due to the extremely small concentrations of bound or free molecules as a result of the comparatively extremely small monolayer surface. Admittedly immobilized membranes do not have the separation problem and also expose an adequate surface, but as a result of the above-described disadvantages are not very flexible and do not form a realistic model system for a membrane.

Thus, the problem of the invention is to make available a novel process which by using solid-supported membranes of lipids or other suitable amphiphilic substances presents the molecule to be analyzed with a substantially biomembrane-analogous surface in a stable, precisely defined arrangement and consequently permits artifact-free, reproducible measurement results. The composition of the solid-supported membranes, compared with immobilized membranes, is to be variable with very limited effort and expenditure and consequently permitting the analysis of specific binding problems on membranes with a complex composition. The mobility of the membrane-forming components by diffusion is maintained despite the coupling to the solid, so that the diffusion processes in biological membranes and the ultrasoft interface between the membrane and aqueous compartment are perfectly imitated. Simultaneously through the presence of the solid, it is very easy to implement separation following incubation with the molecule to be analyzed.

The problem is solved by a process for the analysis of interactions of substances or materials with surfaces or interfaces made from amphiphilic molecules for determining binding constants and/or partition coefficients, in which the amphiphilic molecules arranged in fluid state bilayers are fixed to a carrier as the stationary solid so that the amphiphilic molecules are unimpeded in their lateral diffusion and the substances or materials to be analyzed present in an aqueous, mobile phase and the carrier with the amphiphilic molecules are brought into contact, the carrier with the amphiphilic molecules and the substances or materials interacting therewith are separated from the mobile phase, the concentrations of the substances or materials to be analyzed are determined in the mobile phase and/or in the phase with the carrier, and the interactions of the substances or materials are analyzed and binding constants or partition coefficients are determined as described herein in the appended claims. The problem is further solved by a kit suitable for performing the process according to the invention, as described herein in the appended claims. The wording of all the claims is hereby made by reference into part of the content of the description.

The term "lipids" used in the following text in general terms designates the substance class of lipids (including steroids), as well as lipid-analogous molecules and lipid-similar amphiphiles able, by self-organization processes in a suitable solvent, to form a lipid bilayer or a lipid monolayer.

Bilayers are self-organized, bimolecular layer structures and are produced by swelling lipids in an aqueous medium at temperatures above the phase transition temperature Tm (Sackmann, E. "Polymorphism of Lipid/Water Systems" in "Biophysics" (Hoppe, W., Lohmann, W., Markl, H., Ziegler, H., eds) pp 425, Springer Verlag Berlin, Heidelberg (1983)). Monolayers are self-organized, monomolecular lipid layers, which form spontaneously at an interface between a hydrophilic and a hydrophobic medium.

The term "binding constant" hereinafter is understood to mean a quantity describing the affinity of the membrane surface of the solid-supported membranes (stationary phase) for a substance, which is soluble in the medium surrounding the solid-supported membranes (mobile phase). The term substance relates to any organic or inorganic material which is soluble in the mobile phase. The term "partition coefficient" hereinafter means a quantity which, for a given starting concentration of the substance and for given quantities of solid-supported membrane and mobile phase, quantifies the concentration quotient of the substance between the solid-supported membrane and water compartments present.

For performing the process according to the invention use is made of an inorganic or organic solid, which is coated on its surface with a monomolecular (monolayer) or bimolecular (bilayer) layer of lipids, lipid-analogous molecules or lipid-similar amphiphiles using a process known from the literature, so that its entire surface is completely separated from the medium surrounding it by the monolayer or bilayer (Tamm, L., "Supported Phospholipid Bilayers" Biophysical. Journal (Biophys. Soe. USA), 47, 105–113 (1985), Linseisen, F. M., Hetzer, M., Brumm, T., Bayerl, T. M. "Differences in the physical properties of lipid monolayers and bilayers on a spherical solid support", Biophysical Journal 72, 1659–1667 (1997)). The permanent stabilization of the monolayer or bilayer on the surface can take place either by nonspecific, intermolecular forces (e.g. van-der-Waals or electrostatic forces) or by specific chemical binding to the surface. The coating leads to a biocompatible solid surface, which is referred to hereinafter as solid-supported membrane. The physical and physicochemical characteristics of solid-supported membranes have been described in detail in the literature (Naumann, C. et al. "Phase transition behaviour of single phosphatidylcholine bilayers on a solid support studied by DSC NMR and FT-IR" Biophysical Journal 63, 1314–1319(1992); Bayerl, T. M., Bloom, M. "Physical properties of single phospholipid bilayers adsorbed to microglass beads", Biophysical Journal 58, 357–362 (1990)).

One property of said solid-supported membrane decisive for the process according to the invention is the fact that the latter as the interface to an aqueous medium cannot be distinguished from the side of the medium from a naturally occurring vesicle membrane (e.g. neurotransmitter vesicle) with respect to its physicochemical and biochemical characteristics. This more particularly applies if the molecular lipid composition of the monolayer or bilayer is very close to that of the natural system. Therefore binding processes of molecules dissolved in the aqueous medium at the solid-supported membrane through nonspecific interactions are largely similar to the analogous processes in the natural system.

Adapting to the experimental requirements the lipid composition can be chosen in such a way that the total charge of the coated carrier is neutral or positive/negative charged and a negative charge of the coated carrier is generally preferred.

The determination of the lipid binding constant of the substances dissolved in the aqueous medium (e.g. peptides, proteins, nucleic acids or pharmaceutical agents) at the solid-supported membrane takes place with previously chosen lipid composition obtained by preparation by carrying out a titration series at constant temperature. The temperature is advantageously chosen in such a way that all the lipid components are homogeneously distributed over the solid-supported membrane. This occurs if the temperature is above the chain melting temperature (hereinafter called phase transition temperature (PT) or transition temperature) of the lipids. Under these conditions the membrane is in the so-called fluid state, which also characterizes all biological membranes.

The transition temperature can e.g. be influenced by lowering the pressure. However, it is particularly advantageous to influence the transition temperature by a correspondingly chosen lipid composition.

Advantageously the lipid composition is chosen in such a way that the transition temperature of the amphiphilic molecules is below ambient temperature. In this case the process according to the invention can be performed at ambient temperature and this leads to obvious practical advantages.

Moreover, advantageously by means of an estimate, it is possible to ensure that the solid-supported membrane surface offered during titration is always much larger than the surface required for binding by the substance under analysis, because otherwise saturation effects can disturb or prevent the measurement.

For performing titration either (i) different quantities of the substances to be analyzed for binding purposes are to be titrated in unitary volumes and in vessels always containing the same amount of solid-supported membranes, or (ii) the solid-supported membranes are titrated in different concentrations in the same volumes of vessels containing identical concentrations of the substance to be analyzed. In both cases, advantageously following titration it is ensured (e.g. by an adequately long incubation time or by additionally shaking the vessels), that the partition equilibrium between the membrane-bound and free substances in the individual vessels is obtained. Subsequently, by suitable standard methods (sedimentation, filtration or centrifugation), the solid-supported membranes with the fraction bound thereto of the substance being analyzed are separated from the aqueous solutions in the individual vessels. Separation by filtration is in particular preferred.

In the remaining aqueous solutions, following separation of the solid-supported membranes, for each sample or specimen the concentration of the substance under analysis remaining in the solution is determined. This determination can take place using physicochemical or biochemical standard procedures, which are known from text books and which generally form part of the basic equipment of a modern laboratory. Examples of such methods are optical spectroscopy, infrared spectroscopy, fluorescene spectroscopy and chromatographic methods.

From a consideration of the determined concentrations of the substances for each titration step, using methods known from the literature, it is possible to calculate the lipid binding constant of the substance. Thus, the process permits the rapid determination of a lipid binding constant of a given, water-soluble substance on a membrane with a given lipid position.

It must be borne in mind that the lipid binding constant determined only applies for the lipid composition of the solid-supported membrane used in the titration series. By modifying this lipid composition and repeated measurements it is also possible to determine the optimum lipid composition necessary for the maximum or minimum lipid binding of the given substance.

For a given lipid composition it is also possible to investigate the lipid binding constant of an interesting substance (substance A) under competitive conditions, i.e. in the presence of a second substance (substance B), which by its own interaction with the membrane or with substance A or with both can lead to a change in the lipid binding constant of substance A. The prerequisite for this is that (i) the membrane surface offered during titration is much larger than the surface required by substances A and B for membrane binding and that (ii) the concentration of both substances can be separately determined in the supernatant material. The second condition can e.g. be fulfilled by infrared spectroscopic or chromatographic analysis of the supernatant materials.

In addition, the invention covers the use of carriers, which are coated with amphiphilic molecules in the fluid phase, for analyzing the interactions of substances or materials with surfaces or interfaces made from amphiphilic molecules and from the results obtained conclusions can be drawn concerning the lipophilicity.

The invention also covers a kit suitable for performing the process according to the invention.

The advantages of using solid-supported membranes for determining the lipid binding constants and/or partition coefficients of water-soluble substances or materials compared with the prior art can be summarized in the following way:

1. Through the connection to solids, whose density significantly differs from that of the aqueous medium, the monolayer or bilayer can be easily separated from an aqueous medium using physical methods (e.g. sedimentation, centrifugation, filtration).
2. Another advantage is the precisely quantifiable membrane surface per volume unit when the solid surface is known. This is not possible for free vesicle membranes, because as a result of their immanent instability, they form multilamellar (many bilayer-coated) structures in addition to unilamellar structures (i.e. only one bilayer), so that the membrane surface actually accessible to the dissolved molecule from the aqueous medium is reduced in a not precisely definable way. This can lead to a falsification of the lipid binding constants calculated from such series of measurements.

3. Through the planned choice of solids with a maximized surface/volume ratio (e.g. nanoporous silicates), it is possible to obtain an extremely high proportion of solid-supported membrane surface in a given aqueous volume, which can easily exceed the necessary surface requirement for the binding of substances dissolved in the aqueous volume.
4. Through the coupling of the membrane to the solid, it is ensured that through the binding of the substance to the membrane no morphological changes are induced in the membrane, which can have a feedback to the binding behaviour of the substance. An example of such a change would be the induction of a fusion of "free" membrane vesicles, which is observed with numerous substances and which can be prevented with solid-supported membranes.
5. Solid-supported membranes represent an optimum compromise between physiological relevance on the one hand and high stability and reproducibility on the other. In addition, their lipid composition can be varied with limited technical effort and expenditure and can consequently be very adequately adapted to the specific measurement problem.

The invention also relates to a process for determining the membrane affinity of dissolved substances and materials through the use of solid-supported lipid membranes in column chromatography, particularly high pressure/performance liquid chromatography (HPLC).

In order to characterize lipid affinities of e.g. pharmaceuticals, hitherto use has been made of the approximation of a partition coefficient between the alcohol octanol and water, the so-called Pow value (Fujita, T., Iwasa, J., Hansch, C. "A new substituent constant_, derived from partition coefficients", J. Am. Chem. Soc. 86, 5175–5180, (1994)). Pow can mathematically be obtained from the concentration quotient of the target compound in octanol and water. From the tendency of a compound to stay in the nonpolar alcohol phase, conclusions can be drawn about the lipid solubility thereof. The partition coefficient for readily water-soluble compounds (value range Pow=−2 to 4) can be determined in conventional, chemical manner, i.e. by shaking out between octanol and water and subsequent concentration determination in the adjacent phases (shake flask method).

In the wide value range of Pow=0–6, the standard procedure is to use the high performance liquid chromatography method (HPLC) on nonpolar chromatography materials (so-called reversed phase sorbents). Following the corresponding calibration, this makes it possible to estimate the partition equilibria between octanol and water via retention factors, i.e. via the residence time in the columns up to elution ("Partition Coefficient 10 (n-octanol/water), High Performance Liquid Chromatography (HPLC) Method", OECD Test Guideline 117, 1989). The greater the lipid affinity of a compound the more strongly it is coupled with the hydrophobic chromatography surface of reversed phase materials, i.e. it is eluted later. The octanol-water partition coefficient in adequate manner describes the lipid affinity of nonionized compounds. However, it fails to give reliable information on the membrane binding behaviour of ionized or ionizable molecules representing the largest group of pharmaceutically interesting molecules. Biological membranes are self-organized, heterogeneous objects made from different amphiphilic molecules (mainly lipids), whose complex characteristics can only be very inadequately imitated by the octanol/water interface.

A prerequisite for the exact quantifying of all binding phenomena on biological membranes is consequently precisely defined membrane model systems.

According to the present state of the art for estimating the membrane binding behaviour by means of HPLC processes it is possible to use two different membrane model systems as the stationary phase (sorbents): (I) HPLC silicate-based sorbents on which have been aggregated lipid layers or conglomerates having an undefined structure up to the supersaturation of the surface (Miyake, K., Kitaura, F., Mizuno, N. "Phosphatidyl-choline-coated silica as a stationary phase for high-performance liquid chromatography determination of partition coefficients between octanol and water, Journal of Chromatography, 389, 47–56 (1987)) and (2) so-called immobilized membranes (IAMs), i.e. lipid monolayers fixed on the carrier materials by covalent bonding (Pidgeon, C. "Immobilized Artificial Membranes", U.S. Pat. No. 4,931,498 (1990); Ong, S., Liu, X., Qiu, X., Bhat, G., Pidgeon, C., "Membrane Partition Coefficients Chromatographically Measured Using Immobilized Artificial Membrane Surfaces", Anal. Chem. 67, 755–762 (1995)).

Both systems suffer from significant disadvantages with respect to their usability in HPLC or with respect to their potential for imitating a natural membrane. The stationary phase according to (I) was produced by sources of dipalmitoylphosphatidylcholine (DPPC) in the presence of silicate in an aqueous medium at ambient temperature. However, as the phase transition temperature of DPPC, where the melting of the alkyl chains takes place, is 41° C., as a result of the described production procedure there can only be a completely undefined aggregation of lipids in the form of quasi-crystalline multilayer vesicles and silicate. It is highly probable that the lipid aggregates clog the pores of the silicate gel used and are consequently stabilized in the gel against an extraction through the mobile phase. In the supersaturated state all the pores of the silicate gel are clogged by the lipid aggregates, the surface accessible to the mobile phase largely consists of multilamellar layers of quasi-crystalline DPPC and is consequently largely undefined with respect to the overall surface and the number of lipid layers. It is clear that partition equilibria between water and lipid structures undefined in this way locally differ, i.e. are heterogeneous and consequently represent a fundamental source of error for the determination of the partition coefficient.

Another serious disadvantage for the physiological relevance of this method is that according to (1) it is performed at temperatures below the phase transition temperature of DPPC. Under such conditions the lipid chains are packed in an all-trans conformation and are in a quasi-crystalline order. This represents a significant difference compared with natural membranes, which are always in a disordered and highly mobile, fluid phase. As a result of the approximately 10% larger surface area per lipid in the fluid phase there is also a change to the partition coefficient or the binding constant at the lipid surface. Therefore the result of the measurement according to (I) cannot be directly transferred to the behaviour of a natural membrane.

According to method (2) the lipid molecules are covalently bound via their hydrophobic fatty acid chains to correspondingly preactivated chromatography carriers (e.g. silicate gels). This leads to a completely defined lipid surface, which comprises one lipid monolayer. However, such a better defined surface has been obtained whilst acquiring serious disadvantages. The preparation of IAMs is not only a technically more complicated and therefore more expensive process, but also suffers from the disadvantage of a packing density of the lipids not determined by the intermolecular interaction forces between neighbouring lipids, but by the number of potential binding sites on the carrier material. Therefore the lipid packing density is not precisely defined and is generally lower than in comparable natural membranes. As a result of the covalent fixing a compensation such as exists in fluid membranes through the diffusion of lipids in the membrane plane is impossible here.

For the case of a multicomponent, immobilized lipid mixture the additional disadvantage exists that during the preparation cluster formation of similar lipids can arise through demixing. Consequently corresponding immobilized membranes from complex lipid mixtures can have surface heterogeneities, which falsify the measured result.

The complicated preparation procedure for immobilized membranes also prevents a rapid adaptation of the lipid composition on the surface to the composition desired for the specific experiment.

Thus, the hitherto used HPLC sorbents according to (I) and (2) are only inadequately able to imitate the actual physiological circumstances of a natural membrane and consequently have a considerable error potential when their results are transferred to natural membranes.

Therefore it is an additional problem of the invention, through the use of solid-supported layers of lipids or other suitable amphiphilic substances, to present the molecule to be analyzed with a substantially biomembrane-typical, fluid surface in a stable, geometrically defined arrangement and therefore permit artifact-free, reproducible measured results relevant for natural membranes. The composition of the solid-supported membranes as compared with immobilized membranes is to be variable with very little effort and expenditure and in this way it is possible to analyze specific binding problems on membranes with a complex lipid composition. The mobility of the membrane-forming components by diffusion is to be maintained despite the coupling to the solid, so that the diffusion processes in biological membranes and the ultrasoft interface characteristics between membrane and mobile phase are perfectly imitated. Through the use of a solid as the carrier material and which is suitable for column chromatography, particularly HPLC, membrane-water partition equilibria can be determined with the aid of such efficient methods.

This further problem of the invention is solved by a process for analyzing interactions of substances or materials with surfaces or interfaces made from amphiphilic molecules, particularly for determining binding constants and/or partition coefficients in column chromatography, particularly high performance or pressure liquid chromatography (HPLC), in which amphiphilic molecules in the so-called fluid state are fixed to a carrier as the stationary phase in such a way that the amphiphilic molecules are substantially unimpeded in their lateral diffusion, in which the substances or materials to be analyzed are introduced in a preferably aqueous, mobile phase into the column, which is filled with said carrier, the substances or materials to be analyzed are brought into contact with the carrier in at least one column chromatography run, particularly a HPLC run and the retention times of the substances to be analyzed are determined as described herein in the appended claims. The problem is further solved by providing a material for column chromatography or a correspondingly filled column, which is particularly suitable for performing the process according to the invention, as described herein in the appended claims. By reference, the wording of all these claims is hereby made into part of the content of the description.

For performing the process according to the invention in column chromatography an organic or inorganic solid is surface-coated with a monolayer or bilayer of lipids using procedures known from the literature in such a way that its entire surface is completely separated from the medium surrounding it by the monolayer or bilayer (Tamm, L., "Supported Phospholipid Bilayers" Biophysical Journal (Biophys. Soc. USA) 47, 105–113 (1985), Naumann, C., et al., "Phase transition behaviour of single phosphatidylcholine bilayers on a solid spherical support studied by DSC, NMR and FT-IR", Biophysical Journal 63, 1314–1319 (1992), Linseisen, F. M., Hetzer, M., Brumm, T., Bayerl, T. M. "Differences in the physical properties of lipid monolayers and bilayers on a spherical solid support", Biophysical Journal 72, 1659–1667 (1997)). The process used ensures that said solid is only coated with the bilayer or monolayer and all lipids not required for coating purposes are removed again. The permanent stabilization of the monolayer or bilayer on the surface of the solid takes place through nonspecific, intermolecular forces (e.g. van-der-Waals or electrostatic forces).

For coating purposes lipids are chosen, whose Tm is well below the temperatures at which the measurements (see below) are to be performed. The coating leads to a biocompatible solid surface referred to hereinafter as the solid-supported membrane. The physical and physicochemical characteristics of solid-supported membranes are described in detail in the literature (Naumann, C., et al., "Phase transition behaviour of single phosphatidylcholine bilayers on a solid support studied by DSC, NMR and FR-IR" Biophysical Journal 63, 1314–1319 (1992); Bayerl, T. M., Bloom, M. "Physical properties of single phospholipid bilayers adsorbed to microglass beads", Biophysical Journal 58, 357–362 (1990)).

A decisive characteristic of such solid-supported membranes for the purposes of the process of the invention is the fact that with respect to their physicochemical and biochemical characteristics, as an interface to an aqueous medium, they cannot be distinguished from the side of the medium from a naturally occurring vesicle membrane (e.g. neurotransmitter vesicle). This more particularly applies if the molecular lipid composition of the monolayer or bilayer is similar to that of the natural system. Therefore binding processes of molecules dissolved in the aqueous medium at the solid-supported membrane through unspecific interactions are largely similar to the analogous processes in the natural system.

The determination of the partition coefficient of the substance at the solid-supported membrane with the previously selected lipid composition obtained by preparation takes place through the packing of a defined quantity of solid-supported membranes, preferably in a high performance/pressure liquid chromatography (HPLC) column of suitable dimensions. The packing procedure of such a column does not differ from processes known in chemical and biochemical laboratory practice and is well known to persons trained as laboratory technicians.

Prior to the packing of the column, on the basis of an estimate it is to be ensured that the solid-supported membrane quantity to be packed exposes an overall membrane surface which is much larger than the maximum surface which can be taken up on the solid-supported membrane on adsorbing of a substance to be applied to the column in the next step.

Following the packing of the column, it is initially rinsed with the medium selected for the separation problem (mobile phase) under typical column chromatography conditions, particularly HPLC pressure conditions, until the solid-supported membranes in the column have adapted to the flow through optimum packing and the base line measured by a UV monitor at the column outlet no longer shows any significant time changes (equilibration). The column temperature Ts, as well as the pressure conditions during chromatography must be chosen in such a way that all the lipids contained in the solid-supported membranes are in the fluid state. The term fluid state of the lipids hereinafter is understood to mean the state of molten fatty acid or alkyl chains of the lipids, which is generally reached if Ts is higher than the phase transition temperature Tm of the lipids. Under these conditions the lipids in the monolayer or bilayer are highly mobile and can as a result of lateral diffusion move over the membrane surface (Linseisen, F. M., Hetzer, M., Brumm, T., Bayerl, T. M. "Differences in the physical properties of lipid monolayers and bilayers on a spherical solid support", Biophysical Journal 72, 1659–1667 (1997)), so that there is a homogeneous distribution of the lipid components over the membrane surface.

Following equilibration, a clearly defined quantity of substance to be analyzed is applied to the column, particularly the HPLC column. Under constant, HPLC-typical pressure conditions, measurement takes place of the retention time, i.e. the time elapsing from application to elution of the substance (time tR). This retention time is a measure of the intensity of the interaction between substance and solid phase. The stronger the interaction, the longer the retention time for a given flow rate of the mobile phase or column pressure.

For calibrating the column parameters advantageously subsequently a reference substance is applied to the column and once again the time to its elution is measured (time t0). This reference substance is selected under the standpoint of minimum or negligible affinity for the solid-supported membrane surface. Under these conditions t0 is substantially dependent on the so-called dead volume, which is dependent on the length of the capillaries after the injection block, the geometry of the packing, the porosity of the carrier material and the flow rate or column pressure.

The partition coefficient is calculated from the times tR and t0 using a prior art equation. ("Partition Coefficient (n-octanol/water), High Performance Liquid Chromatography (HPLC) Method", OECD Test Guideline 117, (1989); Kiyake, K., Kitaura, F., Mizuno, N. "Phosphatidylcholine-coated silica as a stationary phase for high-performance liquid chromatography determination of partition coefficients between octanol and water, Journal of Chromatography, 389, 47–56 (1987)). The binding constant can also be calculated with these values using further prior art equations.

The process according to the invention is based on the use of fluid, solid-supported membranes, which are coated with a bilayer or monolayer. Therefore (a) the available membrane surface is precisely defined by the carrier material surface, (b) the membrane is extremely stable against a partial separation of lipids through mechanical forces as a result of the high flow rates of the mobile phase in the column, (c) the solid-supported membrane is very similar to a natural membrane surface through the fluid phase state of the lipid layer and the resulting characteristics and (d) the lipid composition of the solid-supported membrane can be adapted with limited effort to the specific test conditions.

Point (a) is of great significance, because the tests described in the prior art under (1) have shown that a linear correlation between the retention time tR and the octanol/water partition coefficient Pow used in many technical applications only exists above a critical relationship of the carrier material surface to the lipid quantity used for coating. In (1) this critical relationship probably corresponds to a complete clogging of all the pores of the silicate gel with quasi-crystalline DPPC aggregates. In the process according to the invention the critical relationship precisely corresponds to the situation where the complete surface of the carrier material is the same as the complete bilayer or monolayer surface used for coating. Under these conditions a direct interaction of the substance with the carrier surface is no longer possible. The values of the partition coefficient and binding constant are only determined by the interaction at the membrane/mobile phase interface. Whilst this point must be determined for each newly packed column according to the prior art method described under (1), the optimum conditions exist from the outset with the process described here. An overcharging of the column with lipid, such as in part occurs in (I), admittedly relatively reliably leads to a complete covering of the carrier material surface with lipid aggregates, but simultaneously leads to an undefined surface. In addition, the liquid lipids can be slowly detached from the carrier as a result of the mechanical force of the mobile phase flow and can be flushed out of the column. Therefore the available membrane surface would be subject to time changes, which can represent a significant source of error.

Compared with the IAMs described in the prior art under (2), solid-supported bilayers or monolayers also offer decisive advantages. In the case of IAMs the lipids are covalently bound by the hydrophobic end to the carrier, so that a lateral movement of the lipids by diffusion, as is typical for a fluid membrane, is completely prevented. The surface area per lipid in the case of IAMs is not primarily determined by intermolecular interactions between adjacent lipids, but instead by the number of covalent bonding locations for lipids present on the carrier surface. Thus, solid-supported bilayers are more densely packed than IAMs and can also prevent any exposure of the carrier surface to the mobile phase by lateral diffusion. Falsifications of the results are particularly expected with IAMs if the substance has hydrophobic fractions, which tend to be incorporated in the hydrophobic areas of the membrane.

The invention also covers a material for column chromatography, particularly high performance/pressure liquid chromatography, which comprises a preferably pressure-stable carrier, which is coated with amphiphilic molecules in the fluid phase. In the case of the storage or transportation of this material, the carrier coating can also be temporarily transferred into another phase. With respect to the carrier material preference is given to spherical, porous silicate structures, e.g. silicate gels with a 10 or 30 $\mu$m sphere diameter and 400 nm pore size.

The invention finally covers a chromatography column packed with the corresponding material. It is preferably a HPLC column. However, other chromatography columns, such as e.g. FPLC (fast performance liquid chromatography) columns are also covered.

The described features and further features of the invention can be gathered from the following description of examples, in conjunction with the subclaims. The individual features can be implemented individually or in subcombinations.

The following examples constitute specific applications of the process, but do not restrict the general usability thereof.

EXAMPLES

1. Determination of the Lipid Binding Constant of a Completely Purified Model Protein on Lipid Membranes A mixture of 10 mole % anionically charged 1,2-dimyristoyl-sn-glycero-3-phosphatidylglycerol (DMPG), 89.97 mole % zwitterionic lecithin 1,2-dielaidoyl-sn-3- glycero-3-phosphocholine (DEPC) and 0.03 mole % fluorescence marker 1-hexadecanoyl-2-(1-pyrenedecanoyl)-sn-glycero-3-phosphocholine is suspended in chloroform and the solvent completely removed in vacuo. The lipids are subsequently dispersed in aqueous buffer (pH 7.4) and small, unilamellar vesicles are produced by ultrasonic treatment. By mixing with spherical, porous silicate structures (silicate gel with 30 $\mu$m sphere diameter and 400 nm pore size) at temperatures higher than the PT of the mixture, the corresponding solid-supported lipid bilayer is obtained through the spontaneous fusion of the vesicles on the silicate surface. Excess lipid vesicles are removed by sedimentation and separation of the supernatant material. The consistency of the solid-supported membrane, hereinafter called membrane A, is assured with the aid of fluorescence spectroscopy and the composition of the lipid layer is proved by proton NMR spectroscopy.

Membrane A is transferred into buffer A (tris/HCl pH 7.4) and set to a concentration of 0.1 g/ml (roughly corresponds to 5 $\mu$mole lipid bilayer/ml).

In parallel thereto a stock solution of the prepurified model enzyme cytochrome C (4 mg/ml) is also deposited in buffer A and for the titration series in each case 100 $\mu$l double samples or specimens are pipetted into the 1 ml reaction vessels. After adding different quantities of the solid-supported membrane A (20 to 300 $\mu$l) and setting the reaction volume to 1 ml with buffer A, the vessels are incubated for one hour at ambient temperature (bilayer in the fluid state), accompanied by gentle shaking. The solid, biocompatible surface can then be separated from the supernatant material by short, low speed centrifugation (5000×g, duration 10 min).

The free cytochrome C concentration in the supernatant material of each sample of the titration series (15 double samples in all) is determined by UV/Vis absorption measurements at 280 and 410 nm. A corresponding evaluation of the data series gives the lipid binding constant or Kp value of 0.325 mM. The constants obtained correlate very well with literature data of standard binding studies (Heimburg, T., Marsh, D., "Protein Surface-Distribution and Protein—Protein Interactions in the Binding of Peripheral Proteins to Charged Lipid Membranes", Biophysical Journal 68, 536–546 (1995)).

2. Determination of the Lipid Binding Constant of an Approximately Prepurified Protein on Lipid Membranes For this example additionally a solid-supported lipid bilayer with a lipid composition of 20 mole % 1-palmitoyl-2-oleoyl-sn-3-glycero-3-phosphoserine(POPS), 79.97 mole % 1,2-dielaidoyl-sn-3-glycero-3-phosphocholine (DEPC) and 0.03 mole % fluorescence marker 1-hexadecanoy-2-(1-pyrenedecanoyl)-sn-glycero-3-phosphocholine is prepared in accordance with the process described in example 1 on an identical, porous silicate surface. The integrity or completeness of the bilayer coating is proved by fluorescence spectroscopy and the composition of the lipid layer by proton NMR spectroscopy.

The resulting solid-supported membrane from a binary lipid composition is dispersed in buffer B (10 mM tris/HCl, pH 7.4, 1 mM EDTA+protease inhibitor cocktail) and is referred to hereinafter as membrane B.

As the binding partner analysis takes place of the actin-crosslinking brain protein MRP (Hartwig, J. H., Thelen M.; Rosen, A., Janmey, P. A., Nairn, A. C., Aderem, A. A., "MARCKS is an actin filament crosslinking protein regulated by protein kinase C and calcium calmodulin", Nature 356, 618–622 (1992)), which carries a myristoyl side chain. According to the literature (Taniguchi, H., Manenti, S., "Interaction of myristoylated alanine-rich protein kinase C substrate (MARCKS) with membrane phospholipids", J. Biol. Chem. 268 (14), 9960–9963 (1993)), MRP binds with high affinity to the phospholipid phosphatidyl serine anionic at pH 7.4. A solution of constant MRP concentration (prepurified protein) in buffer B is placed in triple samples or specimens in different reaction vessels and mixed with different quantities of membrane A (titration series A) and in analogous manner with membrane B. The incubation and separation of the solid-supported membranes take place as described in example 1.

Aliquot portions of the remaining supernatant materials are analyzed with the aid of SDS polyacrylamide gel electrophoresis (SDS-PAGE), a standard biochemical process. The associated band for the MRP protein is quantified with the aid of a densitometer and the densitometer values are interpreted as MRP concentration values.

The subsequent calculation of the lipid binding constant using standard procedures reveals for the neutral lipid bilayer from titration series A no MRP binding. In titration series B exactly reproducible binding constants are obtained (error<5%) on a bilayer membrane, which additionally contains 20% of POPS anionic at pH 7.4. Thus, the literature-known affinity of MRP for phosphatidyl serine is confirmed by measurements in accordance with the process of the invention and in addition an exact binding constant for the given lipid composition is determined. The data can be rapidly and easily determined and coincide with the measured results of conventional, experimentally much more complicated methods (Vergeres, G., Ramsden, J. J. "Binding of myristoylated alanine-rich C kinase substrate-related protein (MRP) to vesicular phospholipid membranes", Biochem, J. 330, 5–11 (1998)).

3. Determination of the Lipid Binding Constant of a Pharmaceutical

The process for determining lipid binding constants with the aid of solid, biocompatible surfaces can also be used for pharmaceuticals. This is demonstrated here using the example of the local anesthetic tetracaine. For an analyzing the partition coefficient of this pharmaceutical between the lipid and water phases, as described in example 1, porous silicate structures are coated with a charge-neutral membrane of 99.97 mole % zwitterionic lecithin 1,2-dielaidoyl-sn-3-glycero-3-phosphocholine (DEPC) and 0.03 mole % fluorescence marker 1-hexadecanoyl-2-(-pyrenedecanoyl)-sn-glycero-3-phosphocholine (hereinafter called membrane C).

The active agent tetracaine to be analyzed is placed in double sample form in aqueous solution (buffer A) in a constant concentration of 25 $\mu$m and mixed with different quantities of membrane C (concentration range of the lipid $5*10^{-5}-2*10^{-3}$ mole/l). The mixture is incubated for sufficient time to ensure the distribution of the equilibrium. Subsequently the solid, biocompatible surface is removed from the solution by centrifuging or filtration. The free active agent concentration in the supernatant material can be rapidly determined in the case of the UV-active compound tetracaine with the aid of UV/Vis spectroscopy (detection at 304 nm). Alternatively the remaining lipid-free supernatant materials can be analyzed using chromatographic methods (HPLC, gas chromatography, etc.). This once again gives the option of simultaneously analyzing several active agents.

The partition coefficient found for tetracaine between the solid-supported membrane C and the aqueous compartment at the physiologically relevant pH-value 7.4 is 1.4. The binding constants are calculated according to standard procedures.

4. Preparation of a HPLC Column of Solid-Supported Membranes

A natural mixture of egg lecithin and 0.03 mole % fluorescence marker 1-hexadecanoyl-2-(1-pyrenedecanoyl)-sn-glycero-3-phosphocholine is suspended in chloroform and the solvent completely removed in vacuo. The lipids are subsequently dispersed in the aqueous buffer (pH 7.4) and small, unilamellar vesicles are produced by ultrasonic treatment. By mixing with spherical, porous silicate structures (silicate gel with 10 μm sphere diameter and 400 nm pore size) at temperatures higher than the Tm of the lipids, the corresponding solid-supported lipid bilayer is obtained by the spontaneous fusion of the vesicles on the silicate surface. Excess lipid vesicles are removed by sedimentation and separation of the supernatant material. The consistency of the solid-supported bilayer, hereinafter called membrane A1, is assured using fluorescence spectroscopy and analysis of the total carbon content and the composition of the lipid layer is proved by HPLC analysis.

The preparation of the solid-supported monolayer (hereinafter called membrane A2) takes place with the above-used lipid mixture in accordance with the following literature (Linseisen, F. M., Hetzer, M., Brumm, T., Bayerl, T. M. "Differences in the physical properties of lipid monolayers and bilayers on a spherical solid support", Biophysical Journal 72, 1659–1667 (1997)).

Membrane A1 is transferred into buffer A (tris/HCl pH 7.4) and using established procedures is packed in an analytical HPLC column of 150×4 mm and in the precolumn (50×10 mm) (Veronika R. Mayer "Praxis der Hochleistungs-Flssigchromatographie", Verlag M. Diesterweg GmbH, 5th edition, Frankfurt am Main, (1988)). The precolumn is placed between the pump and injector block and the actual analytical column is placed downstream of the injector block. Membrane A2 is packed in the same way in identical HPLC columns.

5. Calibration of a HPLC Column Made from Solid-Supported Membranes

For "starting up" the columns said HPLC systems are rinsed for 60 min at a pressure of approximately 90 bar and a flow rate of 1.8 ml/min. An aqueous buffer system of pH 7.4 serves as the mobile phase (buffer A). In all the further experiments chromatography takes place in the standard way at 23° C., the pressure is 90 bar and the flow rate 1.8 ml/min. Under these conditions the lipids are present in the fluid phase in membranes A1 and A2.

For determining the dead time t0 in the selected system, 5 μl of a 5 mM potassium iodide solution is injected into buffer A. In the case of the HPLC column A1 in reproducible manner a t0 of 0.64 min is measured and for column A2 t0=0.58 min.

Subsequently, for calibration purposes, the columns are charged with eight different reference substances with known Pows in the value range 1 to 4 (acetanilide, benzonitrile, phenol, nitrobenzene, benzene, anisol, toluene and chlorobenzene). When selecting the reference substances it must be ensured that all the compounds are completely in the nonionized state for the mobile phase under the chosen pH conditions. For this case it is to be assumed that the distribution equilibrium between octanol and water in an extremely precise manner also describes the membrane-water distribution, because under these conditions electrostatic interactions between the test substance and the sorption surface can be ignored.

The quantities of compound to be injected are determined on the one hand by its adsorption tendency on the stationary phase and on the other by the detectability of the compound. As a rule most reference compounds can be detected using spectroscopic methods (here UV/V is spectroscopy at 210 nm). The measured retention times tR are directly correlated with the octanol/water partition coefficient using a prior art equation system. The linear dependence makes it possible to calculate regression lines.

The "calibration chromatogram" of the eight reference substances can be very well recorded in the mixture after identifying the individual peaks. The curve obtained is exactly reproducible for 20 successive chromatography runs with columns A1 and A2. The measured standard deviations for tR are always below 0.2 min.

6. Determination of the Membrane-Water Distribution Equilibria of Pharmaceutically Relevant Compounds Pharmaceutically relevant compounds usually have at least one ionizable function. The measured distribution or partition coefficients consequently precisely apply for the defined pH-value under measurement conditions and are reproduced only in an inadequate manner by a mere octanol/water partition coefficient. Distribution equilibria of ionized compounds, unlike those of neutral compounds, are not quantified by means of logP values, but by the pH-dependent logD values. In the present example logD cal-PC, pH 7.4 is determined. The -blocker acetbutolol and the rat poison Warfarin (3-(-acetonylbenzyl)-4-hydroxycoumarin) are in each case dissolved in a concentration of 1 mg/ml in buffer A and in each case 5 æ is injected into columns A1 and A2.

A retention time of tR=4.0 min is reproducibly measured in three successive measurements with column A1 for acetbutolol. From the calibration curve (see 5) can be calculated an associated partition coefficient of logDcal-PC, pH 7.4=2.2. Within an error of 3% identical results are obtained with measurements using column A2. The literature (Betageri, G. V., Rogers J. A., "Thermodynamics of partitioning of -blockers in the n-octanol buffer and liposome systems", Int. J. Pharmaceutics, 36, 165–173 (1987)) gives for the octanol-water distribution of acetbutolol at pH 7.4 a logDow, pH 7.4 of 2.43. For the addition to multilamellar lipid layers of dimyristoylphosphatidylcholine, using extremely time-consuming, cost-intensive experiments (ultracentrifugation) in the fluid phase of the lipids, the authors determine a logDDMPC, pH 7.4 of 2.93. Thus, the present process gives a correct value for the lipid-water distribution equilibrium in an extremely effective, inexpensive manner, unlike in the case of the prior art processes.

Identical information concerning the efficiency and information provided by the present process is given by the comparison experiment with Warfarin. The HPLC method with solid-supported membranes (column A1) reproducibility gives here a retention time of 1.2 min which, according to calibration, corresponds to a logDcal-PC, pH 7.4 of 1.1. The logDow, pH 7.4 for this compound is 0.88. For unilamellar vesicles of dioleoyl phosphatidylcholine (whose analysis once again requires the extremely time-consuming ultracentrifugation), according to the literature a log DDOPC, pH 7.4 of 1.55 is determined (Avdeef, A., Box, K. J., Corner, E. A., Hibbert, C., and K. Y. Tam "pH-Metric logP10. Determination of Liposomal Membrane-Water Partition Coefficients of Ionizable Drugs", Pharmaceutical Research, 15, 209–215 (1998)).

What is claimed is:

1. Process for the analysis of interactions of substances or materials with surfaces or interfaces made from amphiphilic molecules for determining binding constants and/or partition coefficients, in which the amphiphilic molecules arranged in a fluid state bilayer are fixed to a carrier as the stationary solid by nonspecific, intermolecular forces so that the amphiphilic molecules are unimpeded in their lateral diffusion and (a) the substances or materials to be analyzed present in an aqueous, mobile phase and the carrier with the amphiphilic molecules are brought into contact, (b) the carrier with the amphiphilic molecules and the substances or materials interacting therewith are separated from the mobile phase, (c) the concentrations of the substances or materials to be analyzed are determined in the mobile phase and/or in the phase with the carrier, and (d) the interactions of the substances or materials are analyzed and binding constants or partition coefficients are determined.

2. Process according to claim 1, characterized in that the process is performed with a known quantity of substance or material to be analyzed and with a known quantity of stationary solid with the amphiphilic molecules.

3. Process according to claim 1, characterized in that the process is repeatedly performed with different quantities of substance or material to be analyzed or stationary solid with the amphiphilic molecules.

4. Process according to claim 1, characterized in that a partition coefficient is calculated from the concentrations determined according to process step (c).

5. Process according to claim 1, characterized in that a binding constant is calculated from the concentrations determined according to process step (c).

6. Process according to claim 1, characterized in that the process is performed under conditions where the amphiphilic molecules are present in the fluid state, at temperatures above the phase transition temperature of the amphiphilic molecules.

7. Process according to claim 6, characterized in that the phase transition temperature is below 37° C.

8. Process according to claim 1, characterized in that the amphiphilic molecules completely surround the carrier.

9. Process according to claim 1, characterized in that the amphiphilic molecules are lipids.

10. Process according to claim 1, characterized in that a fraction of the amphiphilic molecules are phospholipids.

11. Process according to claim 1, characterized in that the amphiphilic molecules form a layer, in which are present receptors or ligands for the substances or materials to be analyzed.

12. Process according to claim 1, characterized in that the carrier comprises crystalline compounds, silicon, silicon compounds, preferably silicates or glasses, metals, metal films, aluminum, aluminum compounds, titanium, titanium compounds or polymers.

13. Process according to claim 1, characterized in that the carrier is a gel of porous silicate spheres.

14. Process according to claim 1, characterized in that the substances or materials to be analyzed are peptides, proteins, nucleic acids, surfactants, steroids or polymers.

15. Process according to claim 1, characterized in that the substances or materials to be analyzed are pharmaceutical agents or derivatives thereof.

16. Process according to claim 1, characterized in that, apart from the substances or materials to be analyzed, the mobile phase contains further substances or materials.

17. Process according to claim 1, characterized in that the separation of the mobile phase from the stationary solid takes place by sedimentation, centrifugation or filtration.

18. Process according to claim 1, characterized in that the determination of the concentrations of the substances or materials to be analyzed is performed with spectroscopic, chromatographic, chemical, radioactive and/or optical methods.

19. Process according to claim 9, characterized in that the bilayer further contains proteins, peptides, steroids, nucleic acids, ionic or nonionic surfactants, polymers, or mixtures of such substances.

* * * * *